United States Patent [19]
Philippe et al.

[11] Patent Number: 5,665,699
[45] Date of Patent: Sep. 9, 1997

[54] USE OF CERAMIDES AS THICKENERS

[75] Inventors: Michel Philippe, Wissous; Didier Semeria, Courtry; Claude Mahieu, Paris, all of France; Alain Ribier, deceased, late of Paris, France, by Roger Ribier, executor

[73] Assignee: L'Oreal, Paris, France

[21] Appl. No.: 589,461

[22] Filed: Jan. 22, 1996

[30] Foreign Application Priority Data

Jan. 20, 1995 [FR] France ................................ 95-00660

[51] Int. Cl.$^6$ ........................................................ A61K 7/46
[52] U.S. Cl. ........................................................ 512/27
[58] Field of Search ........................................................ 512/27

[56] References Cited

FOREIGN PATENT DOCUMENTS 0 556 957  8/1993  European Pat. Off. .
2 231 871  11/1990  United Kingdom .

OTHER PUBLICATIONS

French Search Report, dated Nov. 27, 1995.

*Primary Examiner*—Terressa Mosley
*Attorney, Agent, or Firm*—Finnegan, Henderson, Farabow, Garrett and Dunner, L.L.P.

[57] ABSTRACT

The use of natural or synthetic ceramides as agents for thickening a medium, particularly a non-aqueous medium, and a thickened medium containing such a thickening agent. The medium thus thickened may be used in the cosmetic, pharmaceutical, paint, varnish, lubricant, combustible, and food industries.

23 Claims, No Drawings

USE OF CERAMIDES AS THICKENERS

The invention relates to the use of natural or synthetic ceramides as agents for thickening media, particularly non-aqueous media.

The agents for thickening media, particularly non-aqueous media, commonly used are N-acylamino acids, such as those described in patent application FR 2,281,162, fatty acid salts, such as the aluminum, magnesium or calcium salts described in U.S. Pat. No. 2,789,329, fatty acid glycerolated esters, fatty esters of dextrin, inorganic colloids such as bentone, or natural products such as beeswax or carnauba wax.

The amino acid derivatives and the fatty acid salts are ionic molecules and therefore are not readily compatible with the mixture of the various adjuvants typically used in the thickening media compositions. Consequently, difficulties in formulating these compositions are encountered when using amino acid derivatives and fatty acid salts. Further, if esters are used, they are generally in the form of a mixture of esters whose proportions are variable and often poorly defined, besides being highly pH sensitive. Consequently, difficulties in formulating the thickening media compositions are also encountered when using esters.

Other agents include synthetic nonionic derivatives, such as 11-N-alkyl-oxycarbonylaminoundecanoic acids and esters thereof, described in patent application FR 2,647,445. These compounds have the drawback of not allowing transparent solutions to be obtained. Further, a certain instability is observed, leading to the appearance of crystals in the thickened solutions containing these agents.

Ceramides in their natural state are the main components of the lipid layers of the epidermis. They can be used in cosmetic compositions, either in natural or synthetic form, to reinforce the barrier effect of the stratum corneum, thereby reducing both water loss and drying out of the skin. See, GB 2,178,312, GB 2,213,723, EP 227,994, EP 282,616, EP 556,957, and U.S. Ser. No. 08/582,978 filed Jan. 4, 1996, the disclosures of which are specifically incorporated by reference herein. Ceramides may also be used in cosmetic compositions for their properties of imparting better elasticity to the skin. See EP 500,437, the disclosure of which is specifically incorporated by reference herein.

The inventors have been able to show, surprisingly and unexpectedly, that natural and synthetic ceramides may be used as agents for thickening a medium. These compounds makes it possible to obtain a thickened medium without the known disadvantages imparted by the thickening agents of the prior art. Because ceramides are compounds usually present in the skin, they have the advantage of not being irritants, making their use in cosmetics desirable.

The subject of the present invention is the use of compounds of formula (I) as agents for thickening media:

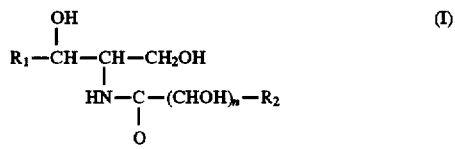

in which $R_1$ represents a saturated or unsaturated linear or branched hydrocarbon radical having from 9 to 25 carbon atoms, $R_2$ represents a saturated or unsaturated linear or branched hydrocarbon radical having from 5 to 29 carbon atoms, and n is 0 or 1. These thickening agents also may be optical isomers, diastereoisomers, mixtures of isomers, or mixtures of the compounds of formula (I).

$R_1$ preferably has from 11 to 23 carbon atoms and $R_2$ preferably has from 7 to 25 carbon atoms. The compounds of formula (I) are preferably: 2-octanoylaminooctadecane-1,3-diol; 2-hexadecanoylaminooctadecane- 1,3-diol; 2-oleoylaminoctadecane-1,3-diol; and 2-tetradecanoylaminooctadecane- 1,3-diol.

These thickeners may be used in the cosmetic, pharmaceutical, paint, varnish, lubricant, combustibles, and food industries.

These compounds have a remarkable thickening property, making it possible to use small amounts of this type of compound in the media to be thickened. These compounds also make it possible to obtain thickened media which display stable homogeneity over time.

The amount of the compounds of formula (I) in the medium to be thickened depends on the desired degree of thickening. As an example, the compounds of formula (I) may be used at concentrations in the range of 0.1% to 20%, preferably in the range of 1% to 10%, by weight relative to the total weight of the medium.

The table below gives a non-limiting example of the proportions of 2-oleoyl-aminooctadecane-1,3-diol necessary to thicken various non-aqueous media:

| | |
|---|---|
| liquid petrolatum (Marcol 82 from Esso) | 2% |
| rapeseed oil (Huilerie de Lapalisse) | 1% |
| miglyol 812 ™ (Dynamit Nobel) | 1% |
| Finsov$_{TN}$ (Witco) | 2% |
| cyclomethicone (cyclopentadimethyl-siloxane from Union Carbide) | 2% |
| 1-(2'-f-hexylethylthio)-3-(2"-ethylhexyloxy)-2-propanol (FR 2,684,668) | 2% |
| Eutanol G (Henkel) | 5% |
| toluene | 2% |
| DMSO:dimethyl sulphoxide | 5% |
| isopropyl myristate | 2% |

The medium may be aqueous but is preferably non-aqueous. When aqueous, it preferably comprises water, a mixture of water and an organic liquid, or an aqueous-alcoholic mixture. When non-aqueous, it may comprise at least one organic liquid including: a saturated or unsaturated hydrocarbon derivative such as, for example, liquid petrolatum, perhydrosqualene, rapeseed oil or jojoba oil; an aliphatic or aromatic fatty ester such as alkyl benzoates, octyl stearate, isopropyl myristate; a triglyceride such as capric and/or caprylic acid triglycerides (miglyol 812™); a polydimethylsiloxane such as cyclomethicone; a fatty alcohol such as octyldodecanol (eutanol G); a solvent such as toluene or dimethyl sulphoxide; or mixtures of two or more of these elements, taken alone or in combination with other non-aqueous components not mentioned above.

The medium may be thickened by completely solubilizing the compound of formula (I) in the medium to be thickened, at a temperature in the range of room temperature to the boiling point of the liquid constituting the medium, followed by allowing the mixture obtained to stand until thickened and preferably until fully thickened. The liquid constituting the medium is preferably an organic liquid.

The thickened medium may constitute or be a constituent of cosmetic or pharmaceutical compositions, paints, varnishes, lubricants, combustibles or food products. The cosmetic or pharmaceutical compositions, paints, varnishes, lubricants, combustibles or food products are preferably non-aqueous. If the thickened medium is used in cosmetic or pharmaceutical compositions, it may, inter alia, be in the form of a stick, milk, or varnish. The present invention includes those ingredients usually used in cosmetic or pharmaceutical compositions. Thus, it may comprise, in particular, at least one additive chosen from fatty alcohols, thickeners, fatty acid esters, fatty acid esters of glycerol, silicones (including volatile or non-volatile and functionalized or non-functionalized silicones), surfactants, fragrances, preserving agents, sunscreens, proteins, vitamins, polymers, and organic or inorganic oils.

All of these compositions are prepared according to the usual methods known to those skilled in the art.

All disclosures of the above references are specifically incorporated herein by reference.

EXAMPLES

Examples of various media thickened by compounds of formula (I), as well as examples of compositions containing them, are illustrated below. These examples should in no way be taken as limiting the scope of the invention.

Example 1

Anhydrous Gel for Very Dry Skin

| | |
|---|---|
| 2-oleoylaminooctadecane-1,3-diol | 5.0% |
| vitamin A palmitate (containing $10^6$ IU/g in peanut oil) | 0.2% |
| tocopheryl acetate | 20.0% |
| liquid petrolatum | 10.0% |
| eutanol G | 34.8% |
| cyclomethicone | 30.0% |

The composition obtained is in the form of a non-flowing gel which can be taken up easily on the fingers. This composition spreads easily over the skin.

Example 2

Thick Anti-aging Fluid

| | |
|---|---|
| 2-oleoylaminooctadecane-1,3-diol | 2.0% |
| vitamin A palmitate (containing $10^6$ IU/g in peanut oil) | 0.5% |
| tocopheryl acetate | 25.5% |
| liquid petrolatum | 12.0% |
| eutanol G | 30.0% |
| cyclomethicone | 30.0% |

This composition is in the form of a fluid cream of moderately thick consistency, which spreads on and penetrates the skin easily.

Example 3

Treating Cream Shampoo

| | |
|---|---|
| 2-oleoylaminooctadecane-1,3-diol | 3.0% |
| alkylpolyglucoside | 10.0% |
| preserving agent | 0.1% |
| water | qs 100.0% |

This shampoo is in the form of a thick cream which is applied directly to the hair. It gives a voluminous mousse and imparts a pleasant feel to the head of hair.

We claim:

1. A method of thickening a medium comprising the step of including in said medium to be thickened an effective amount of at least one compound of formula (I) as an agent for thickening said medium:

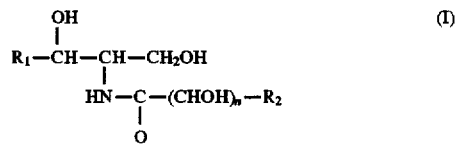

wherein $R_1$ represents a saturated or unsaturated linear or branched hydrocarbon radical containing 9 to 25 carbon atoms, $R_2$ represents a saturated or unsaturated linear or branched hydrocarbon radical containing 5 to 29 carbon atoms, and n is 0 or 1.

2. The method according to claim 1 wherein the agent for thickening the medium is an optical diastereoisomer of the compound of formula (I).

3. The method according to claim 1 wherein the agent for thickening the medium is a mixture of optical diastereoisomers of the compound of formula (I).

4. The method according to claim 1 wherein the medium is non-aqueous.

5. The method according to claim 1 wherein $R_1$ is a hydrocarbon radical containing 11 to 23 carbon atoms.

6. The method according to claim 1 wherein $R_2$ is a hydrocarbon radical containing 7 to 25 carbon atoms.

7. The method according to claim 1 wherein the amount of the compound of formula (I) is in the range of 0.1% to 20% by weight relative to the total weight of the medium.

8. The method according to claim 7 wherein the amount of the compound of formula (I) is in the range of 1% to 10% by weight relative to the total weight of the medium.

9. The method according to claim 1 wherein the compound of formula (I) is 2-octanoylaminooctadecane-1,3-diol, 2-hexadecanoylaminooctadecane-1,3-diol, 2-oleoylaminooctadecane-1,3-diol, or 2-tetradecanoylaminooctadecane-1,3-diol.

10. The method according to claim 4 wherein the non-aqueous medium comprises at least one saturated or unsaturated hydrocarbon compound, aliphatic or aromatic fatty ester, triglyceride, polydimethylsiloxane, alcohol, or solvent.

11. The method according to claim 4 wherein the non-aqueous medium comprises at least one liquid petrolatum, perhydrosqualene, rapeseed oil, jojoba oil, aliphatic or aromatic fatty esters, octyl stearate, isopropyl myristate, triglycerides, polydimethylsiloxanes, fatty alcohols, or solvents.

12. The method according to claim 11 wherein the aliphatic or aromatic fatty ester is an alkyl benzoate, the triglyceride is capric or caprylic triglyceride, the polydimethylsiloxane is cyclomethicone, the fatty alcohol is octyldodecanol, and the solvent is toluene or dimethyl sulphoxide.

13. A process for thickening a medium comprising the steps of:

solubilizing at least one compound of formula (I):

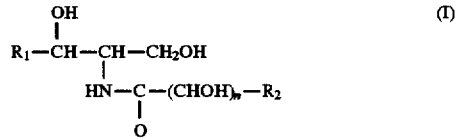

wherein $R_1$ represents a saturated or unsaturated linear or branched hydrocarbon radical containing 9 to 25 carbon atoms, $R_2$ represents a saturated or unsaturated linear or branched hydrocarbon radical containing 5 to 29 carbon atoms, and n is 0 or 1;

in a liquid medium to be thickened at a temperature in the range of room temperature to the boiling point of said liquid medium; and then letting the mixture stand until thickened.

14. The process according to claim 13 wherein the liquid medium is organic.

15. A thickened liquid medium comprising a liquid medium and an amount effective to thicken said medium of at least one compound of formula (I):

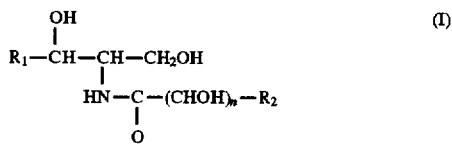

wherein $R_1$ represents a saturated or unsaturated linear or branched hydrocarbon radical containing 9 to 25 carbon atoms, $R_2$ represents a saturated or unsaturated linear or branched hydrocarbon radical containing 5 to 29 carbon atoms, and n is 0 or 1.

16. The thickened liquid medium according to claim 15 wherein the compound is at least one optical diastereoisomer of the compound of formula (I).

17. The thickened liquid medium according to claim 15 wherein $R_1$ is a hydrocarbon radical containing 11 to 23 carbon atoms.

18. The thickened liquid medium according to claim 15 wherein $R_2$ is a hydrocarbon radical containing 7 to 25 carbon atoms.

19. The thickened liquid medium according to claim 15 wherein the amount of the compound of formula (I) is in the range of 0.1% to 20% by weight relative to the total weight of the medium.

20. The thickened liquid medium according to claim 19 wherein the amount of the compound of formula (I) is in the range of 1% to 10% by weight relative to the total weight of the medium.

21. A cosmetic, pharmaceutical, paint, varnish, lubricant, combustible, or food product containing the thickened liquid medium of claim 15.

22. A cosmetic or pharmaceutical product containing the thickened liquid medium of claim 15.

23. The thickened liquid medium according to claim 15 wherein said liquid medium is non-aqueous.

* * * * *

UNITED STATES PATENT AND TRADEMARK OFFICE
CERTIFICATE OF CORRECTION

PATENT NO. : 5,665,699
DATED : September 9, 1997
INVENTOR(S) : Michel PHILIPPE et al.

It is certified that error appears in the above-identified patent and that said Letters Patent is hereby corrected as shown below:

In the Claims, claim 1, column 4, in Formula (I) change "C" to --C--;
$$\begin{array}{cc} | & \| \\ O & O \end{array}$$

claim 13, column 4, in Formula (I) change "C" to --C--;
$$\begin{array}{cc} | & \| \\ O & O \end{array}$$

claim 15, column 5, in Formula (I) change "C" to --C--;
$$\begin{array}{cc} | & \| \\ O & O \end{array}$$

Signed and Sealed this

Second Day of December, 1997

*Attest:*

BRUCE LEHMAN

*Attesting Officer*    Commissioner of Patents and Trademarks